(12) United States Patent
Govari

(10) Patent No.: US 11,510,692 B2
(45) Date of Patent: *Nov. 29, 2022

(54) EAR-NOSE-THROAT (ENT) NAVIGABLE SHAVER WITH FERROMAGNETIC COMPONENTS

(71) Applicant: Biosense Webster (Israel) Ltd., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 434 days.

This patent is subject to a terminal disclaimer.

(21) Appl. No.: 16/427,833

(22) Filed: May 31, 2019

(65) Prior Publication Data

US 2020/0375617 A1    Dec. 3, 2020

(51) Int. Cl.
| | |
|---|---|
| *A61B 17/24* | (2006.01) |
| *A61B 34/20* | (2016.01) |
| *A61B 1/233* | (2006.01) |
| *A61B 5/06* | (2006.01) |
| *A61M 25/00* | (2006.01) |

(52) U.S. Cl.
CPC .............. *A61B 17/24* (2013.01); *A61B 1/233* (2013.01); *A61B 5/062* (2013.01); *A61B 34/20* (2016.02); *A61M 25/0041* (2013.01); *A61B 2034/2046* (2016.02); *A61B 2034/2051* (2016.02); *A61M 2210/0681* (2013.01)

(58) Field of Classification Search
CPC ......... A61B 17/24; A61B 34/20; A61B 1/233; A61B 5/062; A61B 2034/2051; A61B 2034/2046; A61B 2034/2072; A61B 2017/00725; A61B 2017/00119; A61M 25/0041; A61M 2210/0681
See application file for complete search history.

(56) References Cited

U.S. PATENT DOCUMENTS

| | | |
|---|---|---|
| 5,391,199 A | 2/1995 | Ben-Haim |
| 6,239,724 B1 | 5/2001 | Doron et al. |

(Continued)

OTHER PUBLICATIONS

International Search Report dated Aug. 24, 2020 from corresponding PCT Patent Application No. PCT/IB2020/054417.

(Continued)

*Primary Examiner* — Sean D Mattson
(74) *Attorney, Agent, or Firm* — Frost Brown Todd LLC

(57) ABSTRACT

A system includes a medical probe and a position-tracking system. The medical probe includes a distal end, and one or more distal magnetic position sensors. The medical probe further includes a proximal-end assembly, and one or more proximal magnetic position sensors. The position-tracking system includes a memory, which is configured to hold values indicative of known relative positions between the distal magnetic position sensors and the proximal magnetic position sensors. The position-tracking system includes a processor, which is configured to receive one or more signals indicative of estimated positions of the proximal magnetic position sensors and of the distal magnetic position sensors, as measured by the position-tracking system, and to initiate a responsive action in response to detecting a discrepancy between the known relative positions and the estimated positions.

21 Claims, 3 Drawing Sheets

(56) References Cited

U.S. PATENT DOCUMENTS

| | | | |
|---|---|---|---|
| 6,272,371 B1* | 8/2001 | Shlomo | A61M 25/01 |
| | | | 600/424 |
| 6,332,089 B1 | 12/2001 | Acker et al. | |
| 6,484,118 B1 | 11/2002 | Govari | |
| 6,618,612 B1 | 9/2003 | Acker et al. | |
| 6,690,963 B2 | 2/2004 | Ben-Haim et al. | |
| 9,333,047 B2* | 5/2016 | Mucha | A61B 34/30 |
| 10,952,797 B2* | 3/2021 | Govari | A61B 34/20 |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2006/0122497 A1* | 6/2006 | Glossop | A61B 34/20 |
| | | | 600/424 |
| 2007/0208252 A1* | 9/2007 | Makower | A61B 6/037 |
| | | | 600/424 |
| 2008/0121703 A1* | 5/2008 | Li | G16Z 99/00 |
| | | | 235/385 |
| 2009/0115406 A1* | 5/2009 | Anderson | A61B 34/20 |
| | | | 324/207.17 |
| 2011/0308536 A1* | 12/2011 | Govari | A61B 34/20 |
| | | | 128/899 |
| 2014/0187915 A1* | 7/2014 | Yaroshenko | A61B 6/54 |
| | | | 600/424 |
| 2018/0280049 A1 | 10/2018 | Algawi et al. | |

OTHER PUBLICATIONS

U.S. Appl. No. 15/859,969, filed Jan. 2, 2018, entitled "Tracking a Rigid Tool in a Patient Body".

* cited by examiner

EAR-NOSE-THROAT (ENT) NAVIGABLE SHAVER WITH FERROMAGNETIC COMPONENTS

FIELD OF THE INVENTION

The present invention relates generally to invasive medical probes, and particularly to methods and systems for tracking a medical probe in a patient body.

BACKGROUND OF THE INVENTION

Techniques for tracking a medical probe inside a cavity of an organ of a patient were previously proposed in the patent literature. For example, U.S. Patent Application Publication 2018/0280049, issued as U.S. Pat. No. 10,537,350 on Jan. 21, 2020, describes a medical device that includes a disposable Ear-Nose-Throat (ENT) tool, a reusable handle, and a processor. The ENT tool is configured to perform a medical procedure in a patient ENT organ. The reusable handle is configured to hold and control the disposable ENT tool, and includes a position sensor configured to produce one or more position signals that are indicative of a first position of the reusable handle. The processor is configured to receive the position signals from the position sensor, and to estimate, based on the position signals, a second position of the disposable ENT tool in the patient ENT organ.

As another example, U.S. Pat. No. 6,272,371 describes an invasive probe apparatus including flexible elongate probe having a distal portion adjacent to a distal end thereof for insertion into the body of a subject. The distal portion assumes a predetermined curve form when a force is applied thereto. First and second sensors are fixed to the distal portion of the probe in known positions relative to the distal end, which sensors generate signals responsive to bending of the probe. Signal processing circuitry receives the bend responsive signals and processes them to find position and orientation coordinates of at least the first sensor, and to determine the locations of a plurality of points along the length of the distal portion of the probe.

SUMMARY OF THE INVENTION

An embodiment of the present invention provides a system, including a medical probe and a position-tracking system. The medical probe includes a distal end, and one or more distal magnetic position sensors coupled to the distal end. The medical probe further includes a proximal-end assembly, and one or more proximal magnetic position sensors coupled to the proximal-end assembly. The position-tracking system includes a memory, which is configured to hold values indicative of known relative positions between the distal magnetic position sensors and the proximal magnetic position sensors. The position-tracking system includes a processor, which is configured to receive one or more signals indicative of estimated positions of the proximal magnetic position sensors and of the distal magnetic position sensors, as measured by the position-tracking system, and to initiate a responsive action in response to detecting a discrepancy between the known relative positions and the estimated positions.

In some embodiments, the distal end includes a part that causes a change in a magnetic field crossing the distal end. In some embodiments, the part that causes the change in the magnetic field includes a ferromagnetic material.

In some embodiments, the distal position sensors are coupled to a shaft of the medical probe, and wherein the proximal magnetic position sensors are coupled to a handle of the medical probe.

In an embodiment, the shaft is rotating and the processor is configured to detect the discrepancy based on values generated by the one or more rotating distal magnetic position sensors.

In another embodiment, the processor is configured to correct the detected discrepancy based on the values indicative of the known relative positions.

In some embodiments, the processor is configured to alert a user to the detected discrepancy.

In some embodiments, the processor is configured to compare between the values indicative of the known relative positions and values of the estimated positions so as to detect the discrepancy.

In an embodiment, the medical probe includes an ear-nose-throat (ENT) tool.

There is additionally provided, in accordance with an embodiment of the present invention, a method, including inserting into an organ of a patient a medical probe including (a) a distal end, (b) one or more distal magnetic position sensors coupled to the distal end, (c) a proximal-end assembly, and (d) one or more proximal magnetic position sensors coupled to the proximal-end assembly. The distal end is tracked using a position-tracking system, by (i) holding values indicative of known relative positions between the distal magnetic position sensors and the proximal magnetic position sensors, (ii) receiving one or more signals indicative of estimated positions of the proximal magnetic position sensors and of the distal magnetic position sensors, as measured by the position-tracking system, and (iii) initiating a responsive action in response to detecting a discrepancy between the known relative positions and the estimated positions.

There is further provided, in accordance with an embodiment of the present invention, a medical probe, including a distal end, one or more distal magnetic position sensors, a proximal-end assembly, and one or more proximal magnetic position sensors. The one or more distal magnetic position sensors are coupled to the distal end. The one or more proximal magnetic position sensors are coupled to the proximal-end assembly.

The present invention will be more fully understood from the following detailed description of the embodiments thereof, taken together with the drawings in which:

DETAILED DESCRIPTION OF EMBODIMENTS

Overview

Figure 1:
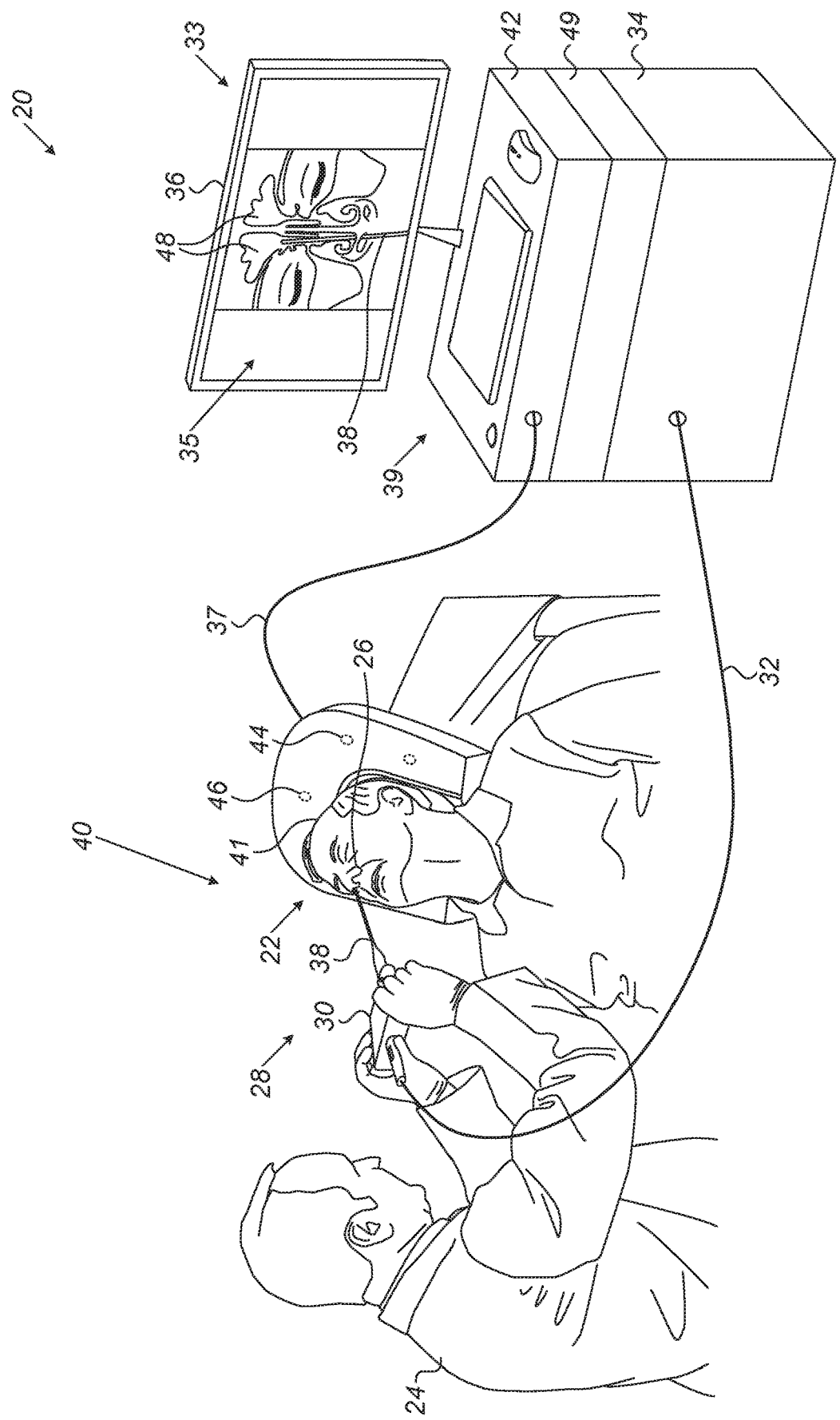
FIG. 1 is a schematic, pictorial illustration of an ear-nose-throat (ENT) procedure using an ENT module comprising a navigable shaver, in accordance with an embodiment of the present invention.

Some medical procedures require navigating a distal end of a medical probe inside a cavity of an organ of a patient.

For example, ear-nose-throat (ENT) procedures may require navigating an ENT navigable shaver inserted into the sinuses of a patient's head.

In principle, the distal end of the probe may be tracked inside the patient body by coupling multiple position sensors of a magnetic position-tracking system to the distal end. The position measurements may be calibrated by applying a predefined magnetic field using the magnetic position-tracking system and, based on position signals acquired during a medical procedure, a processor may estimate the positions of the position sensors.

An apparatus comprising an ENT probe with multiple position sensors of a magnetic position-tracking system that are coupled to a distal end of the ENT probe, is described in U.S. patent application Ser. No. 15/859,969, filed Jan. 2, 2018, entitled "Tracking a Rigid Tool in a Patient Body," issued as U.S. Pat. No. 10,952,797 on Mar. 23, 2021, which is assigned to the assignee of the present patent application and whose disclosure is incorporated herein by reference.

In some cases, however, the magnetic field inside the cavity of the organ may be distorted by some mechanism, e.g., by ferromagnetic parts of the distal end of the probe itself. If the distortion caused to the magnetic field is not taken into consideration, the distortion may degrade the tracking accuracy of the medical probe in the patient organ. Moreover, where there is a rotating distal end, the rotation of the distal position sensors may by itself (e.g., via rotating electrical fields), or further to any ferromagnetic parts, distort the position signals they generate.

Embodiments of the present invention that are described hereinbelow provide improved techniques for tracking a medical probe, such as an ENT tool comprising a part that causes a change (e.g., distortion) in a magnetic field crossing the distal end, inside a patient organ. In some embodiments, a proximal end (e.g., the handle) of the disclosed medical probe comprises one or more proximal position sensors, and the distal end of the medical probe comprises one or more distal position sensors.

The one or more proximal position sensors, which are attached to parts of the probe that are less affected by the ferromagnetic parts of the distal end, give an indication of the position and orientation of the distal end. The one or more distal position sensors fitted to the distal end generate possibly-distorted position signals, which hinder accurate position tracking of the distal end.

Since the medical probe is rigid, each of the distal position sensors maintains a fixed known position relative to the proximal position sensors during the procedure. In some embodiments, using the geometrically known relative positions among the multiple position sensors (i.e., the physical relationship between the distal and proximal sensors), together with the indication from the proximal sensors, the processor detects, constrains, and corrects the distorted measurements by the distal sensors to derive an improved indication of the position and orientation of the distal end.

In an embodiment, the positions of the one or more distal position sensors relative to the positions of the one or more proximal position sensors are stored in a memory accessed by the processor.

In some embodiments, the processor is configured to correct the distorted distal position measurements by the position-tracking system by comparing the resulting estimated relative positions of the various sensors to the geometrically known relative positions of the sensors.

In some embodiments, the processor is configured to initiate a suitable responsive action, such as alerting the physician, in response to detecting a discrepancy between the known positions of the distal position sensors relative to the proximal position sensors and estimated positions.

Typically, the processor is programmed in software containing a particular algorithm that enables the processor to conduct each of the processor-related steps and functions outlined above.

The disclosed techniques enable improved quality of minimally invasive medical procedures by allowing magnetic position tracking of medical probes comprising ferromagnetic parts, without compromising the accuracy in tracking the positions of the involved probes.

System Description

FIG. 1 is a schematic, pictorial illustration of an ear-nose-throat (ENT) procedure using ENT module 28 comprising a navigable shaver, in accordance with an embodiment of the present invention. In some embodiments, an ENT system 20, which comprises ENT module 28, is configured to carry out an ENT procedure, such as treating an infection from one or more sinuses 48 of a patient 22.

In some embodiments, ENT module 28 comprises an ENT distal end 38 comprising the shaver tool at its distal end (shaver tool not shown), which a physician 24 inserts into a nose 26 of patient 22. Module 28 further comprises a handheld proximal-end assembly 30, coupled to a proximal end of distal end 38, which is configured to assist physician 24 to navigate distal end 38 in a head 41 of patient 22.

In an embodiment, system 20 further comprises a magnetic position-tracking system, which is configured to track the position of multiple position sensors in, and in the vicinity of, head 41. The magnetic position-tracking system comprises magnetic field generators 44 and multiple position sensors shown in FIG. 2 below. The position sensors generate position signals in response to sensing external magnetic fields generated by field generators 44, thereby enabling a processor 34 to estimate the position of each sensor, as will be described below.

This method of position sensing is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, issued as U.S. Pat. No. 6,690,963 on Feb. 10, 2004; 2003/0120150 A1, issued as U.S. Pat. No. 7,729,742 on Jun. 1, 2010; and 2004/0068178 A1, now abandoned, whose disclosures are all incorporated herein by reference.

System 20 further comprises a location pad 40, which comprises field generators 44 fixed on a frame 46. In the exemplary configuration shown in FIG. 1, pad 40 comprises five field generators 44, but may alternatively comprise any other suitable number of generators 44. Pad 40 further comprises a pillow (not shown) placed under head 41 of patient 22, such that generators 44 are located at fixed, known positions external to head 41.

In some embodiments, system 20 comprises a console 33, which comprises a memory 49, and a driver circuit 42 configured to drive field generators 44, via a cable 37, with suitable signals so as to generate magnetic fields in a predefined working volume in space around head 41.

In some embodiments, console 33 comprises a processor 34, typically a general purpose computer, with suitable front end and interface circuits for receiving signals from ENT module 28 having multiple magnetic sensors coupled thereto (shown in FIG. 2 below), via a cable 32, and for controlling other components of system 20 described herein.

In some embodiments, processor 34 is configured to estimate the position of each position sensor. Based on the estimated positions of the sensors, processor 34 is configured to derive the position and orientation of distal end 38 in the coordinate system of the magnetic position-tracking system.

In some embodiments, processor 34 is configured to receive, via an interface (not shown), one or more anatomical images, such as computerized tomography (CT) images depicting respective segmented two-dimensional (2D) slices of head 41, obtained using an external CT system (not shown). The term "segmented" refers to displaying various types of tissue identified in each slice by measuring respective attenuation of the tissues in the CT system.

Console 33 further comprises input devices 39 for controlling the operation of the console, and a user display 36, which is configured to display the data (e.g., images) received from processor 34 and/or to display inputs inserted by a user using input devices 39 (e.g., by physician 24).

In some embodiments, processor 34 is configured to select one or mode slices from the CT images, such as an image 35, and to display the selected slice on user display 36. In the example of FIG. 1, image 35 depicts a sectional front-view of one or more sinuses 48 of patient 22.

FIG. 1 shows only elements related to the disclosed techniques, for the sake of simplicity and clarity. System 20 typically comprises additional modules and elements that are not directly related to the disclosed techniques, and thus, are intentionally omitted from FIG. 1 and from the corresponding description.

Processor 34 may be programmed in software to carry out the functions that are used by the system, and to store data in memory 49 to be processed or otherwise used by the software. The software may be downloaded to the processor in electronic form, over a network, for example, or it may be provided on non-transitory tangible media, such as optical, magnetic or electronic memory media. Alternatively, some or all of the functions of processor 34 may be carried out by dedicated or programmable digital hardware components. In particular, processor 34 runs a dedicated algorithm as disclosed herein, including in FIG. 3, that enables processor 34 to perform the disclosed steps, as further described below.

ENT Navigable Shaver With Ferromagnetic Components

Figure 2:
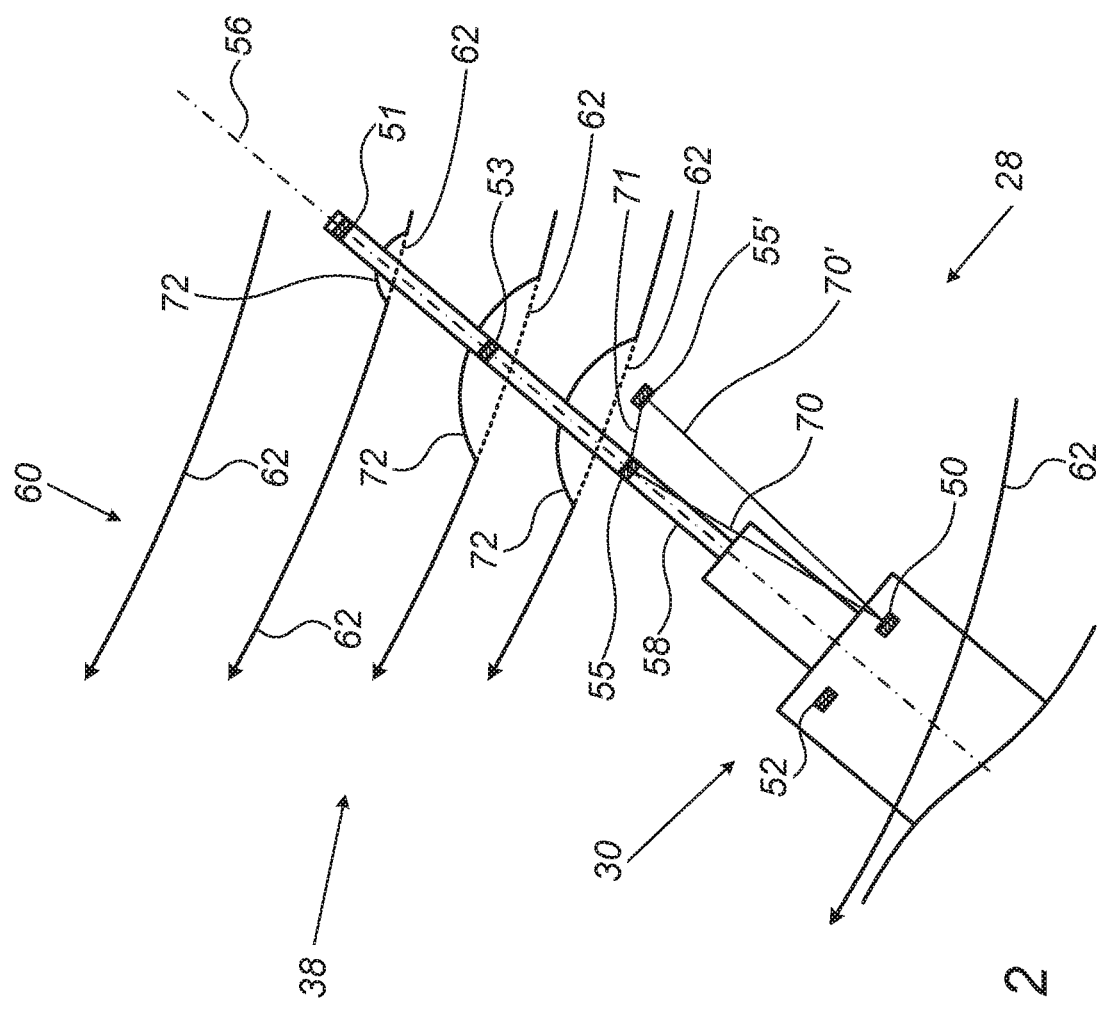
FIG. 2 is a schematic, pictorial illustration of the ENT module applied in the ENT procedure of FIG. 1, in accordance with an embodiment of the present invention.

FIG. 2 is a schematic, pictorial illustration of ENT module 28 applied in the ENT procedure of FIG. 1, in accordance with an embodiment of the present invention.

In some embodiments, ENT module 28 comprises one or more proximal magnetic position sensors, in the present example two sensors denoted 50 and 52, coupled at known positions over handheld proximal-end assembly 30. Distal end 38 comprises one or more distal magnetic position sensors, in the present example three sensors denoted 51, 53, and 55, coupled at known positions over distal end 38, for example along a longitudinal axis 56 of a shaft 58. In the shown embodiment, shaft 58 of the navigational shaver comprises ferromagnetic material.

In the context of the present disclosure, the term "known positions" refers to the actual positions of sensors 50 and 52 relative to a predefined coordinate system of system 20.

In an embodiment, distal end 38 may have a straight form, as shown for example in FIG. 2. Geometrically known positions of distal position sensors 51, 53, 55 relative to sensors 50 and 52 may be defined by a set of vectors 70, of which one vector, between sensors 55 and 50, is shown in FIG. 2.

In other embodiments, any other suitable definition and measurement may be applied to obtain the known relative positions. For example, where the distal end has a curved or irregular shape, the relative positions of the distal sensors along the curved shape may be used to better estimate the distal positions.

In some embodiments, the known relative positions of distal position sensors 51, 53, and 55, relative to proximal sensors 50 and 52, are stored in memory 49 of system 20. The known relative positions may be provided, for example, by the ENT module manufacturer.

In some embodiments, during the ENT procedure, magnetic field generators 44 apply a magnetic field 60 shown by magnetic field lines 62. Based on signals received from position sensors 51, 53, and 55, processor 34 estimates the position of each of distal position sensors 51, 53, and 55 in the coordinate system of the magnetic position-tracking system.

However, due to the ferromagnetic material in shaft 58, magnetic field lines 62 in the vicinity of the shaft (shown in dashed lines in FIG. 2) are locally distorted into curved magnetic field lines 72. Proximal position sensors 50 and 52 are unaffected by distorted magnetic field lines 72, and their position is therefore accurately measured by system 20.

In some embodiments, processor 34 is configured to calculate, based on the estimated distal positions, respective estimated positions of sensors 51, 53, and 55 relative to the measured positions of sensors 50 and 52. The estimated relative positions may be defined, for example, as vectors 70 known from the geometry of ENT module 28.

In some embodiments, processor 34 stores (in memory 49 or in a memory of processor 34) a threshold value for determining whether a discrepancy exists between a given known vector, such as vector 70, and a corresponding estimated vector that is wrong, as position of sensor 55 is wrongly estimated as 55' due to distorted lines 72, such as vector 70'. Examples of threshold values may be a norm, such as a distance 71 that equals the norm $\|70\text{-}70'\|$, and/or an angle. The threshold value that determines the discrepancy may be different among at least two of the known vectors, or alternatively, may be similar for all known vectors.

In some embodiments, tool 38 is calibrated with respect to one or more predefined magnetic fields, typically before conducting the procedure, so as to minimize the initial discrepancy levels.

In some embodiments, processor 34 may initiate a responsive action when detecting the discrepancy between an estimated distance and known distance, such as when norm $\|70\text{-}70'\|$ has a value above a given threshold.

In an embodiment, in applying the responsive action, processor 34 may display an alert message to physician 24, e.g., on display 36, to delay the ENT procedure.

In some embodiments, after correcting the distorted position measurements of distal sensors 51, 53, and 55, processor 34 displays, e.g., on user display 36, a message indicating that the distorted position measurements have been corrected successfully so that physician 24 may proceed with the ENT procedure.

The configuration of system ENT module 28 is depicted by way of example for the sake of conceptual clarity. In other embodiments, any alternative configuration may be used, for example, the number of distal and proximal position sensors, and the distances and directions between each couple of the position sensors may vary, so as to comply with various requirements, such as medical, regulatory, or technical requirements.

Figure 3:
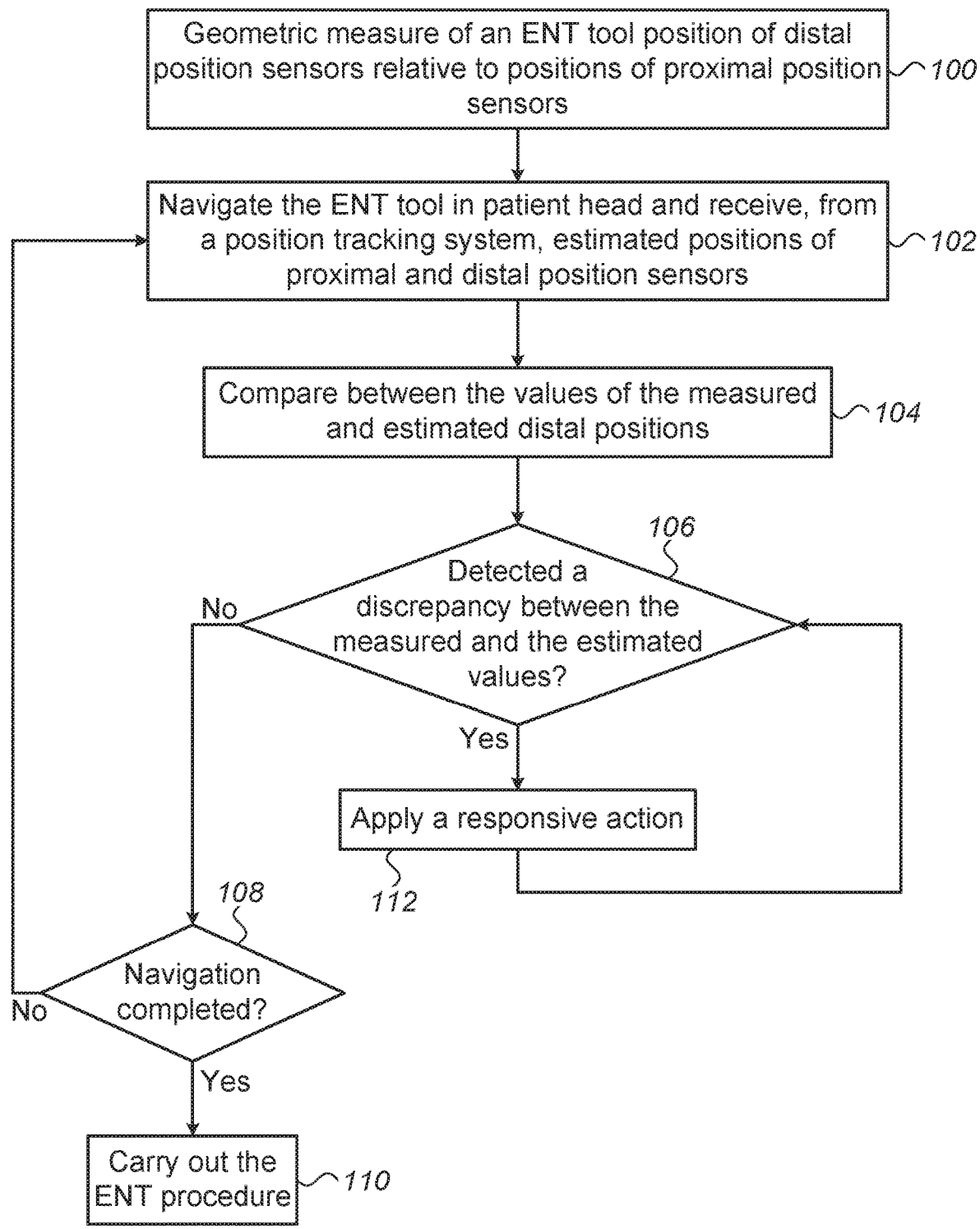
FIG. 3 is a flow chart that schematically illustrates a method and algorithm for tracking the distal end of the ENT module of FIG. 2 in a patient head, in accordance with an embodiment of the present invention.

FIG. 3 is a flow chart that schematically illustrates a method and algorithm for tracking distal end 38 of the ENT module 28 of FIG. 2 in patient head 41, in accordance with an embodiment of the present invention. The method begins at a physical measurement step 100, in which, for example, a technician geometrically measures, over ENT module 28, positions of distal position sensors 51, 53, and 55, relative to positions of proximal position sensors 50 and 52, such as vector 70 depicted in FIG. 2 above, before conducting the ENT procedure. In some embodiments, the technician, or another user, stores vectors 70 in memory 49 of console 33.

At a tool navigation step 102, physician 24 inserts the navigational shaver that is fitted on ENT distal end into patient head 41 and receives the estimated positions of sensors 51, 53, and 55 from processor 34, based on signal measured by the position-tracking system.

At a comparison step 104, processor 34 compares, using the dedicated disclosed algorithm, calculated vectors 70' and measured vectors 70 (i.e., compares distal positions relative to proximal positions), so as to detect whether there is a discrepancy (e.g., above one or more predefined thresholds) related to the positions of the distal sensors relative to the proximal sensors.

In other embodiments, processor 34 may compare the measured distal positions to the estimated relative positions of sensors 51, 53, and 55 using any other suitable technique, rather than comparing between the known and estimated vectors.

At a discrepancy detection step 106, processor 34 checks for discrepancies between any of the measured (i.e., known) relative position values stored in memory 49, and the estimated relative position values obtained based on the positions of sensors 51, 53, and 55 measured by the position-tracking system.

If no discrepancy is detected, the method proceeds to a navigation completion step 108, in which processor 34 or physician 24 checks whether ENT distal end 38 is positioned at the target location in head 41, so that physician 24 may apply the navigable shaver to carry out the ENT procedure.

If a discrepancy is detected, the method is routed to a responsive action step 112, in which processor 34 notifies physician 24 of the detected discrepancy and, optionally, conducts one or more corrective actions, such as correcting the distorted position measurements carried out by sensors 51, as described in FIG. 2 above.

In other embodiments, processor 34 may recommend an action to the user by displaying a suitable message, and/or physician 24 may decide to terminate the procedure and retract ENT distal end 38 from the body of patient 22, as part of the responsive actions conducted in step 112.

If processor 34 corrects the distorted position measurements carried out by sensors 51, 53, and 55, the method loops back to detection step 106, in which processor 34 checks whether all the discrepancies detected in step 106 are corrected, e.g., are now below the predefined threshold.

In case all the discrepancies are corrected, the method is routed to navigation completion step 108 so as to check whether ENT distal end 38 is positioned at the target location, or whether the method loops back to navigation step 102.

If the navigation is completed, the method is routed to an ENT procedure step 110, which terminates the method. At step 110, the navigable shaver is positioned at the target location in head 41 (e.g., sinus 48) and physician 24 may carry out the ENT procedure, such as applying the ENT navigable shaver for removal of an infected portion of sinus 48.

Although the embodiments described herein mainly address ENT procedures, the methods and systems described herein can also be used in other applications that require magnetically tracking a position and/or orientation of a medical device comprising ferromagnetic materials, such as in otolaryngology, cardiology, or neurology.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
    (a) a medical probe, comprising:
        (i) a distal end,
        (ii) one or more distal magnetic position sensors coupled to the distal end and configured to generate one or more distal position signals,
        (iii) a proximal-end assembly, and
        (iv) one or more proximal magnetic position sensors coupled to the proximal-end assembly and configured to generate one or more proximal position signals; and
    (b) a position-tracking system, comprising:
        (i) a memory, which is configured to hold values indicative of known relative positions between the one or more distal magnetic position sensors and the one or more proximal magnetic position sensors, and
        (ii) a processor, which is configured to:
            (A) determine, estimated positions of the one or more proximal magnetic position sensors based on the one or more proximal position signals,
            (B) determine estimated positions of the one or more distal magnetic position sensors based on the one or more distal position signals,
            (C) determine geometric positions of the one or more distal magnetic position sensors based on the estimated positions of the one or more proximal magnetic positions sensors and the known relative positions between the one or more distal magnetic position sensors and the one or more proximal magnetic position sensors, and
            (D) initiate a responsive action in response to detecting a discrepancy between the estimated positions of the one or more distal magnetic position sensors and the geometric positions of the one or more distal magnetic position sensors.

2. The system according to claim 1, wherein the distal end comprises a part that is configured to cause a change in a magnetic field crossing the distal end.

3. The system according to claim 2, wherein the part that is configured to cause the change in the magnetic field comprises a ferromagnetic material.

4. The system according to claim 1, wherein the one or more distal magnetic position sensors are coupled to a shaft of the medical probe, and wherein the one or more proximal magnetic position sensors are coupled to a handle of the medical probe.

5. The system according to claim 4, wherein the shaft is rotatable, and wherein the processor is configured to detect the discrepancy based on values generated by rotating the one or more distal magnetic position sensors.

6. The system according to claim 1, wherein initiating the responsive action in response to detecting the discrepancy comprises correcting the detected discrepancy based on the values indicative of the known relative positions.

7. The system according to claim 1, wherein initiating the responsive action in response to detecting the discrepancy comprises alerting a user to the detected discrepancy.

8. The system according to claim 1, wherein the processor is configured to compare a difference between the estimated positions of the one or more distal magnetic position sensors and the geometric positions of the one or more distal magnetic position sensors with a threshold so as to detect the discrepancy.

9. The system according to claim 1, wherein the medical probe comprises an ear-nose-throat (ENT) tool.

10. A method, comprising:
(a) inserting into an organ of a patient a medical probe comprising:
  (i) a distal end,
  (ii) one or more distal magnetic position sensors coupled to the distal end,
  (iii) a proximal-end assembly, and
  (iv) one or more proximal magnetic position sensors coupled to the proximal-end assembly; and
(b) tracking the distal end using a position-tracking system, by:
  (i) holding values indicative of known relative positions between the one or more distal magnetic position sensors and the one or more proximal magnetic position sensors,
  (ii) receiving, from the one or more proximal magnetic position sensors, one or more proximal position signals indicative of estimated positions of the one or more proximal magnetic position sensors,
  (iii) receiving, from the one or more distal magnetic position sensors, one or more distal position signals indicative of estimated positions of the one or more distal magnetic position sensors,
  (iv) determining the estimated positions of the one or more proximal magnetic position sensors based on the one or more proximal position signals;
  (v) determining the estimated positions of the one or more distal magnetic position sensors based on the one or more distal position signals;
  (vi) determining geometric positions of the one or more distal magnetic position sensors based on the estimated positions of the one or more proximal magnetic position sensors and the known relative positions between the one or more distal magnetic position sensors and the one or more proximal magnetic position sensors, and
  (vii) initiating a responsive action in response to detecting a discrepancy between the estimated positions of the one or more distal magnetic position sensors and the geometric positions of the one or more distal magnetic position sensors.

11. The method according to claim 10, wherein the distal end comprises a part that causes a change in a magnetic field crossing the distal end.

12. The method according to claim 11, wherein the part that causes the change in the magnetic field comprises a ferromagnetic material.

13. The method according to claim 10, wherein the one or more distal magnetic position sensors are coupled to a shaft of the medical probe, and wherein the one or more proximal magnetic position sensors are coupled to a handle of the medical probe.

14. The method according to claim 13, further comprising rotating the shaft, wherein detecting the discrepancy comprises detecting the discrepancy based on values generated by the one or more distal magnetic position sensors that are coupled to the shaft that is rotating.

15. The method according to claim 10, wherein initiating the responsive action comprises correcting the detected discrepancy based on the values indicative of the known relative positions.

16. The method according to claim 10, wherein initiating the responsive action comprises alerting a user to the detected discrepancy.

17. The method according to claim 10, wherein detecting the discrepancy comprises comparing a difference between the estimated positions of the one or more distal magnetic position sensors and the geometric positions of the one or more distal magnetic position sensors with a threshold.

18. The method according to claim 10, wherein the medical probe comprises an ear-nose-throat (ENT) tool, and wherein the one or more distal magnetic position sensors are coupled along a longitudinal axis of the ENT tool.

19. A medical probe, comprising:
(a) a distal end;
(b) one or more distal magnetic position sensors coupled to the distal end, the one or more distal magnetic position sensors being configured to provide signals indicating a first estimated position to a navigational system;
(c) a proximal-end assembly; and
(d) one or more proximal magnetic position sensors coupled to the proximal-end assembly, the one or more proximal magnetic position sensors being configured to provide signals indicating a second estimated position to the navigational system;
wherein the navigational system is configured to initiate a responsive action in response to detecting a discrepancy between a geometric position and the first estimated position, wherein the geometric position is based on the second estimated position and a known relative position between the one or more distal magnetic position sensors and the one or more proximal magnetic position sensors.

20. The medical probe according to claim 19, wherein the distal end comprises a part that is configured to cause a change in a magnetic field crossing the distal end.

21. The medical probe according to claim 20, wherein the part that is configured to cause the change in the magnetic field comprises a ferromagnetic material.

* * * * *